(12) United States Patent
Khanuja et al.

(10) Patent No.: US 6,676,974 B2
(45) Date of Patent: Jan. 13, 2004

(54) **BIOACTIVE HEXANE FRACTION FROM *VETIVERIA ZIZANIOIDES***

(75) Inventors: Suman Preet Singh Khanuja, Lucknow (IN); Suchi Srivastava, Lucknow (IN); Tiruppadiripuliyur Ranganathan Santha Kumar, Lucknow (IN); Madan Mohan Gupta, Lucknow (IN); Arvind Kumar Tripathy, Lucknow (IN); Monika Singh, Luckinow (IN); Janak Raj Bahl, Lucknow (IN); Raj Kishori Lal, Lucknow (IN); Mahendra Pandurang Darokar, Lucknow (IN); Ajit Kumar Shasany, Lucknow (IN); Sushil Kumar, Lucknow (IN)

(73) Assignee: Council of Scientific and Industrial Research, New Dehli (IN)

( * ) Notice: Subject to any disclaimer, the term of this patent is extended or adjusted under 35 U.S.C. 154(b) by 0 days.

(21) Appl. No.: 10/105,794

(22) Filed: Mar. 26, 2002

(65) Prior Publication Data

US 2003/0198698 A1 Oct. 23, 2003

(51) Int. Cl.⁷ ............................................... A01N 59/06

(52) U.S. Cl. ........................ 424/686; 424/692; 424/715; 424/725; 424/750

(58) Field of Search ................................. 424/715, 725, 424/750, 686, 692

(56) References Cited

U.S. PATENT DOCUMENTS

| | | | | |
|---|---|---|---|---|
| 4,293,602 A | * | 10/1981 | Coffey et al. ................. | 428/28 |
| 4,937,073 A | * | 6/1990 | Fujikura et al. ............ | 424/750 |
| 6,193,976 B1 | * | 2/2001 | Porras et al. ................ | 424/750 |

* cited by examiner

Primary Examiner—Herbert J. Lilling
(74) Attorney, Agent, or Firm—Nixon Peabody LLP; Donald R. Studebaker

(57) ABSTRACT

The present invention relates a hexane bioactive fraction and obtained from the roots of an aromatic plant named *Vetiveria zizanioides* commonly found in India for inhibiting the growth of drug resistant bacterial infections in humans and animals; also relates to a pharmaceutical composition comprising the bioactive extract with other additives for inhibiting the growth of drug resistant bacterial infections in humans and animals and a process for the isolation of said bioactive extract

23 Claims, No Drawings

BIOACTIVE HEXANE FRACTION FROM *VETIVERIA ZIZANIOIDES*

FIELD OF THE INVENTION

The present invention relates a hexane bioactive fraction and obtained from the roots of an aromatic plant named *Vetiveria zizanioides* commonly found in India for inhibiting the growth of drug resistant bacterial infections in humans and animals. The invention also relates to a pharmaceutical composition comprising the bioactive extract with other additives for inhibiting the growth of drug resistant bacterial infections in humans and animals. The present invention also provides a process for the isolation of said bioactive extract.

BACKGROUND OF INVENTION

Antibiotics have been used for long to cure bacterial, fungal and other infectious diseases of humans. Penicillin was the first antibiotic used against infections during the Second World War. Since then a number of antibiotics and their derivatives have been identified and used by man almost all of which were isolated from microbial sources. All the antibiotics in clinical use today can be grouped or classified according to their structure or functional groups. Streptomycin, kanamycin, tetracycline some of the well-known examples are aminoglycosides whereas penicillin and its derivatives are beta-lactam antibiotics. One of the commonly used antibacterials are quinolones or fluoroquinolones such as nalidixic acid, ciprofloxacin, norfloxacin etc. Fluoroquinolones are now widely used to treat urinary tract infections, upper respiratory tract infections, and tuberculosis, which are resistant to first-line drugs. However, many of the pathogenic bacteria such as *Haemophilus influenzae*, Neisseria Sp., *Staphylococcus aureus*, *Escherichia coli* are developing resistance to fluoroquinolone class of antibiotics limiting their clinical usefulness. Since, the mechanism of action of all the quinolones against bacteria is similar, development of resistance to one of the quinolone antibiotic would confer simultaneous cross-resistance to almost all the other quinolones also. Fluoroquinolones act by inhibiting the function of a bacterial enzyme DNA gyrase essential for the maintenance of supercoil nature of the bacterial chromosome. Resistance development is observed when a mutation in the DNA gyrase enzyme A subunit (GyrA+) specifically in the region called "Quinolone Determining Region (QDR)" occurs. The modified mutant form of A subunit (GyrA−) is incapable of binding to quinolone antibiotics and therefore is resistant. Such quinolone resistant infections are particularly difficult to cure. Kumar et al (*Phytotherapy Research*14: 14–15, 2000; U.S. Pat. No. 6,127,405) have identified a semi-synthetic plant compound α-arteether which is capable of specifically killing quinolone drug resistant bacterial infections. The α-arteether was obtained by etherification of artemissinin a sesquiterpene lactone compound from a Chinese medicinal plant *Artemisia annua*. In our effort to isolate and identify more potent plant compounds which are active against quinolone resistant bacteria we carried out a systematic bioactivity guided fractionation of the ethanolic extract prepared from the roots of Indian medicinal plant *Vetiveria zizanioides*. The subject mentioned below specifically describes the manner in which the compound inhibiting quinolone resistant bacteria was isolated and identified.

OBJECTS OF THE INVENTION

The main object of the invention is to develop a novel anti bacterial agent inhibiting the growth of multi drug resistant bacterial pathogens.

Another object of the invention is to provide a bioactive fraction from the roots of plant *Vetiveria zizanioides*.

Another object of the invention is to provide a pharmaceutical composition comprising bioactive fraction or plant extract obtained from plant *Vetiveria zizanioides*

Still another object of the invention is to provide a method of isolation of bioactive fraction from the roots of plant *Vetiveria zizanioides*.

SUMMARY OF THE INVENTION

Accordingly, the present invention provides a bioactive hexane fraction named as CIM 109 obtained from the roots of plant *Vetiveria zizanioides* for inhibiting growth of multidrug resistant bacterial pathogens. The present invention also provides a pharmaceutical composition comprising bioactive fraction CIM 109 or plant extract or lyophilised extract to provide anti bacterial activity.

DETAILED DESCRIPTION OF INVENTION

Accordingly, the present invention provides a bioactive hexane fraction CIM 109 obtained from the plant *Vetiveria zizaniodes* having inhibitory activity against multi drug resistant bacterial pathogens.

One embodiment of the invention, the said bioactive fraction inhibits the growth of bacterial pathogens which are resistant to nalidixic acid, oxolinic acid, sparfloxicin, ciprofloxicin, lomefloxicin and any other quinolones.

Another embodiment of the invention, the multidrug resistant bacteria is selected from the group consisting of genus Mycobacterium or *Escherchia coli* preferably selected from group consisting of *Mucobacterium smegmatis* $MC^2155$, *Pseudomonas aeruginosa*, *Bacillus subtilis* MTCC-121, *Mucobacterium smegmatis* $MC^2155$ Wld type, *Mucobacterium smegmatis* $MC^2155$ (NaiR) 6b, *Mucobacterium smegmatis* $MC^2155$ 13a and *E.Coli* DH5a.

One more embodiment of the invention relates to a pharmaceutical composition for inhibiting the growth of the bacterial pathogens, comprising effective amount of bioactive fraction named CIM-109 or partially purified extract or lyophilised extract, obtained from the plant *Vetiveria zizanioides*.

Another embodiment of the invention, the composition containing the said bioactive fraction is used singly or in combination thereof to the patient.

Still another embodiment, the composition may be administered systematically or orally and preferably orally.

Still another embodiment, the bioactive fraction is administered to the patient in combination with a pharmaceutically acceptable additives carriers, diluent, solvent, filter, lubricant, excipient, binder or stabiliser.

Yet another embodiment relates to the additive used which is selected from a group consisting of citric acid, calcium carbonate, magnesium hydroxide gel and/or gel and/or lactose.

Yet another embodiment relates to amount of active fraction in the composition is in the range of 100 mg to 500 mg.

Yet another embodiment of the invention relates to amount of composition administered to a subject is in the range of 500 mg to 1000 mg per day.

Yet another embodiment of the invention relates to amount of composition administered to a subject is preferably in the range of 150 mg to 700 mg per day.

Yet another embodiment of the invention, the subject is selected mammals, animals preferably humans.

In another embodiment of the invention provides a pharmaceutical composition useful for treating fluoroquinolone resistant bacterial infections including entenc and systemic infections, said composition comprising 10 to 50% by wt of root extract of vetiver, 0.4 to 1% by wt of citric acid, 10 to 20% by wt of calcium carbonate, 10 to 20% by wt of magnesium hydroxide gel, 20 to 60% by weight of lactose and optionally comprising other pharmaceutically acceptable additives. The above said composition can optionally compounded with honey by dispersing the constituents in honey.

One more embodiment of the invention relates to a method of treating patients with bacterial infection said method comprising administering a pharmaceutically effective dosage of bioactive fraction or a formulation comprising bioactive fraction or lyophilized extract of plant *Vetiveria zizanioides* thereof to the patient.

Another embodiment of the invention relates to a process for the isolation of bioactive fraction from the plant *Vetiveria zizaniodes* having inhibitory activity against multi drug resistant bacterial pathogens, the said process comprises steps of:

a) powdering the plant part of *Vetivera Zizanioides*, b) extracting the plant powder of step (a) by soaking in protic aqueous organic solvent for a period of 16–20 hours, c) filtering the organic solvent extract of step (b), d) evaporating the extract of step (c) under reduced pressure to remove the organic solvent to obtain an aqueous extract, e) lyophilizing the aqueous extract of step (d) to get a powered extract, f) dissolving the powdered extract of step (e) in 2% aqueous citric acid, g) extracting the solution of step (f) successively with chloroform, n-butanol, methanol and finally with acetone to obtain respective organic extracts and an aqueous solution, h) evaporating separately the organic extracts of step (g) to obtain respective residues, i) neutralizing the aqueous solution of step (g) with ammonia solution, j) testing the bioactivity of residues obtained in step (h) and neutralized solution of step (i) to identify residue from methanolic extract as bioactive residue, k) macerating the residue of methanoloic extract of step (h) successively with hexane, chloroform and ethylacetate, l) testing bioactivity of hexane, chloroform and ethylacetate fractions of step (k) to identify hexane fractions as a bioactive fraction, m) purifying the residue of hexane fraction of step (l) on a silica gel column using eluant hexane and mixture of hexane-chloroform with increasing polarity, and n) evaporating the hexane-chloroform (1:1) eluant fraction obtained from step (m) to yield a residue, which is purified by thin layer chromatography to achieve the required bioactive fraction.

Another embodiment of the invention, in which the bioactive fraction obtained in step (m), is designated as CIM 109.

Still another embodiment of the invention provides a bioactive fraction obtained from roots of *Vetivera Zizanioides*.

Still another embodiment of the invention, the protic aqueous organic solvent used in step (b) theis selected from aqueous alcohol preferably aqueous ethanol.

In our study specifically directed at finding an antibiotic or plant compound, which can specifically kill quinolone drug resistant bacterial infections, we found that the ethanolic extract of roots of *Vetiveria zizanioides* was able to kill GyrA– mutant *E.coli* bacteria but not the wild type strains (GyrA+). The ethanolic extract was then fractionated by liquid-liquid chromatography and the hexane fraction was to found to possess the growth inhibitory activity. The hexane fraction was then fractionated using silica gel column chromatography wherein the fraction eluted using 10% Chloroform in hexane indicated the desired bioactivity of eliminating *Mycobacterium smegmatis* (GyrA–) growth. Further to isolate and purify the active principle the eluted 10% chloroform in hexane fraction was separated by column chromatography. The Chl:Hex (50:50) fraction obtained from this column was able kill the GyrA– strains of *E.coli* and *M.smegmatis* bacteria. The Chl:Hex (50:50) fraction was then purified by thin layer chromatography (TLC) to obtain a pure fraction called CIM 109 which has shown the desired bioactivty. Thus CIM 109 isolated from the roots of *Vetiveria zizanioides* was able to inhibit the growth of fluoro-quinolone resistant (GyrA–) bacteria. Hence, CIM 109 can be used for treating quinolone resistant bacterial infections of human and animals.

The detailed description of the invention is explained in the form of examples and should not construed to limit the scope of the invention.

EXAMPLE-1

The roots of *Vetiveria zizanioides* genotype KS-1 grown in CIMAP farm harvested during the month of April was dried in shade and ground to fine powder and then extracted by dipping the plant material overnight in different solvents. The solvent was then evaporated in vacuo and the residue termed as root extracts was redissolved in dimethylsulfoxide (DMSO) at the required concentration and analysed for bioactivity.

EXAMPLE-2

The ethanolic extracted prepared as above was tested for their growth inhibitory property against a number of bacterial strains by disc diffusion assay a procedure commonly followed and can be performed by persons skilled in the art. The results indicated that the ethanolic extracted residue showed a surprisingly interesting inhibitory activity against many bacterial strains. Hence, to explore the potential of using the extracts as anti-microbial agents the ethanolic extracted was then fractionated using different solvents as follows:

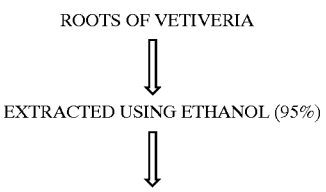

ROOTS OF VETIVERIA

⇓

EXTRACTED USING ETHANOL (95%)

⇓

-continued

LYOPHILIZED POWDER DISSOLVED IN
2% citric acid in water

⇓

LIQUID-LIQUID FRACTIONATION USING VARIOUS SOLVENTS

1. CHLOROFORM FRACTION
2. BUTANOL FRACTION
3. METHANOL FRACTION
4. ACETONE FRACTION
5. CITRIC ACID FRACTION IN WATER AFTER NEUTRALISATION WITH AMMONIA SOLUTION

⇓

BIOACTIVITY TESTING OF ALL FRACTIONS

⇓

POSITIVE FRACTION (METHANOL) FURTHER FRACTIONATED USING SOLVENTS LIKE HEXANE, ETHYL, ACETATE AND CHLOROFORM.

⇓

BIOACTIVITY TESTING OF ALL FRACTIONS

⇓

HEXANE FRACTION WAS FOUND TO BE ACTIVE SILICA GEL COLUMN CHROMATOGRAPHY AS IN EXAMPLE-5

EXAMPLE-3

The ethanolic extract of the roots of *Vetiveria zizanioides* was further fractionated by liquid—liquid chromatography using different solvents. The extracts were initially dissolved in citric acid containing water and the solvent extraction was performed with increasing degree of polarity. The solvent extracts obtained were then evaporated in vacuo and the residues were analysed for their anti-microbial activity by disc diffusion assays. The results as in table-1 indicate that the methanolic fraction exhibited maximum bioactivity against bacterial pathogens. We observed an interesting feature that the methanolic fraction does not inhibit the growth of wild type *E.coli* starin CA8000 but was inhibitory to the nalidixic acid resistant strains of *E.coli* DH5a, NK5819 and ET8000. These strains were resistant to nalidixic acid by virtue of carrying mutations in the gyrA gene, which also confers resistance to other flouroquinolones (FQ) such as ciprofloxacin, norfloxacin, levofloxacin etc. Hence we hypothesised that the methanolic extract might contain some active principle, which is able to specifically kill the FQ resistant bacteria but not the normal sensitive bacteria such as CA8000. Therefore to isolate the biologically active principle fraction, the applicants resorted to column chromatography of the methanolic fraction of the ethanolic root extract of *Vetiveria zizanioides* KS-1.

TABLE-1

Bioactivity Response of different solvent fractions of the root extracts of *Vetiveria zizanioides* on different Bacterial Strains added @ 0.8 mg/disc.

| Strains | Zone of growth inhibition (mm) | | |
|---|---|---|---|
| | Methanol | Spirit | Citric Acid |
| *Salmonella typhimurium* | 2 | 2 | — |
| *Mycobacterium smegmatis* MC$^2$ 155 | 4 | 2 | 1 |
| *Pseudomonas aeruginosa* | 7 | 6 | 9 |
| *Bacillus subtilis* MTCC-121 | 1 | | |
| *E.coli* CA8000 | — | — | — |
| *E.coli* DH5 | 2 | — | — |
| *E.coli* NK5819 | 2 | — | — |
| *E.coli* ET8000 | 2 | — | — |

EXAMPLE-4

Further to test whether the active principle present in the methanolic can inhibit the growth of Mycobacterium sp. we fractionated the methanolic extract using three different solvents by liquid—liquid chromatography a commonly used technique which a person skilled in the art can perform. The bioactivity testing against *Mycobacterium smegmatis* strain Mc$^2$155 results showed that the hexane, chloroform and methanol fractions were inhibitory to the nalidixic acid resistant strains (NalR) (6b and 13a) of *Mycobacterium smegmatis* strain Mc$^2$155 but not the wild type.

TABLE-2

Bioactivity response (zone of growth inhibition) of liquid-liquid fractions of the methanolic extract of *Vetiveria zizanioides* KS-1 on *M. smegmatis*.

| | *Mycobacterium smegmatis* strain Mc$^2$155 (wld type) | *Mycobacterium smegmatis* strain Mc$^2$155 (Na1R) 6b | *Mycobacterium smegmatis* strain Mc$^2$155 13a |
|---|---|---|---|
| Hex fraction | — | 10 mm | 4 mm |
| Ethyl acetate | — | — | — |
| Chloroform | — | 5 mm | 3 mm |
| Meth. Fraction | — | 6 mm | 15 mm |

Hence, it is clear from the above observation that the active principle not only inhibits the growth of FQ resistant *E.coli* strains as in example-3 but also inhibits the growth of the FQ resistant *Mycobacterium smegmatis* strain 6b and 13a specifically.

EXAMPLE-5

Further to purify the active principle silica gel column chromatography was performed. Any person who is skilled in the art of related subjects can perform the technique. About 20 g of hexane fraction was packed onto a silica gel column and the fractions were eluted in hexane—chloroform solvent system. The table-3 below gives the number of column fractions collected using each solvent system. The column fractions were subsequently analysed for their inhibitory activity against *M.smegmatis* wild type and the mutants resistant to nalidixic acid. The results indicate that the column fractions eluted using 10% Hexane in chloroform was able to inhibit only the nalidixic acid resistant strains of *M.smegmatis* and not the wild type bacteria whereas the 15% and 25% Hexane in chloroform was able to inhibit both the wild type and Nal R mutant indicating that it is non specific. Moreover the 60% Hexane:Chloroform fraction was able to inhibit the NalR strains of *E.coli* but not the wild type. Therefore the 10–60% hexane in chloroform fraction can inhibit the fluoroquinolone resistant strains of both *E.coli* and *M.smegmatis* and therefore possess the ability to cure such drug resistant infections in humans and animals.

| Solvent system used | Amount of each fraction collected | No. of fractions collected | No. of fractions collected |
|---|---|---|---|
| Hexane | 100 ml | 20 | 2 lit. |
| 10% CHCl₃ in Hexane | 100 ml | 150 | 15 lit. |
| 15% CnCl₃ in Hexane | 100 ml | 15 × 5 = 75 | 7.5 lit. |
| 25% CHCl₃ in Hexane | 100 ml | 16 × 4 = 64 | 8 lit. |
| 30% CHCl₃ in Hexane | 100 ml | 8 × 4 = 32 | 4 lit. |
| 35% CHCl₃ in Hexane | 100 ml | 10 × 4 = 40 | 5 lit. |
| 40% CHCl₃ in Hexane | 100 ml | 10 × 4 = 40 | 5 lit. |
| 50% CHCl₃ in Hexane | 100 ml | 6 × 4 = 24 | 3 lit. |
| 75% CHCl₃ in Hexane | 100 ml | 16 × 4 = 64 | 8 lit. |
| CHCl₃ fraction | 100 ml | 13 × 4 = 52 | 7 lit. |
| 5% Eto Ac | 100 ml | 8 × 4 = 32 | 4 lit. |
| 10% Eto Ac | 100 ml | 6 × 4 = 24 | 3 lit. |
| 20% Eto Ac | 100 ml | 4 × 4 = 16 | 2 lit. |
| 30% Eto Ac | 100 ml | 4 × 4 = 16 | 2 lit. |
| 50% Eto Ac | 100 ml | 4 × 4 = 16 | 2 lit. |

Bioactivity Profile of Various Column Chromatography Fractions Against *M.smegmatis* and the Nal R Mutant 6b.

| | | Range of Zone of growth inhibition (400 mcg/disc) | |
|---|---|---|---|
| | Solvent system used | *M.smegmatis* | *E.coli* |
| Fraction No. | for the elution | (wild type) | 6b (na1R) | DH5a |
| 0 1-6 | 10% Hex.:Chl. | — | — | — |
| OY-6 | 25% Hex.:Chl. | 3–5 | 5–10 | — |
| OY-11 | 15% Hex.:Chl. | 2–5 | 7–24 | — |
| LY-11 | 30% Hex.:Chl. | 2–5 | 2–18 | 3–4 |
| | 60% Hex: Chl | | 2–10 | |
| CIM-109 | TLC purified fraction | | 12–15 | 6–8 |

What is claimed is:

1. A process for the isolation of bioactive fraction of the plant *Vetivera zizanioides* comprising the steps of:
   a) powdering the plant part of *Vetivera zizanioides*,
   b) extracting the plant powder of step (a) by soaking in protic aqueous organic solvent for a period of 16–20 hours,
   c) filtering the organic solvent extract of step (b),
   d) evaporating the extract of step (c) under reduced pressure to remove the organic solvent to obtain an aqueous extract,
   e) lyophilising the aqueous extract of step (d) to get an powdered extract,
   f) dissolving the powdered extract of step (e) in 2% aqueous citric acid,
   g) extracting the solution of step (f) successively with chloroform, n-butanol, methanol and finally with acetone to obtain respective organic extracts and an aqueous solution,
   h) evaporating separately the organic extracts of step (g) to obtain respective residues,
   i) neutralizing the aqueous solution of step (g) with ammonia solution,
   j) testing the bioactivity of residues obtained in step (h) and neutralized solution of step (i) to identify residue from methanolic extract as bioactive residue,
   k) macerating the residue of methanoloic extract of step (h) successively with hexane, chloroform and ethylacetate,
   l) testing bioactivity of hexane, chloroform ethylacetate fractions of step (k) to identify hexane fractions as a bioactive fraction,
   m) purifying the residue of hexane faction of step (l) on a silica gel column using eluant hexane and mixture of hexane-chloroform with increasing polarity, and
   n) evaporating the hexane-choroform (1:1) eluant fraction obtained from step (m) to yield a residue, which is purified by thin layer chromatography to achieve the required bioactive fraction.

2. The process as claimed in claim 1, wherein the bioactive fraction obtained in step (m) is designated as CIM 109.

3. The process as claimed in claim 1, wherein the plant part is selected from roots of *Vetivera zizanioides*.

4. The process as claimed in claim 1, wherein in step (b) the protic aqueous organic solvent is aqueous ethanol.

5. A bioactive hexane fraction obtained from the plant *Vetiveria zizanioides* having inhibitory activity against multi drug resistant bacterial pathogens, said bioactive hexane fraction being obtained by the process of claim 1.

6. The bioactive fraction as claimed in claim 5, the said bioactive fraction inhibits the growth of bacterial pathogens which are resistant to nalidixic acid, oxolinic acid, sparfioxicin, ciprofloxicin, lomefloxicin and any other quinolones.

7. The bioactive fraction as claimed in claim 6, wherein multidrug resistant bacteria is selected from the group consisting of genus Mycobacterium or *Escherchia coli* preferably selected from the group consisting of *Mucobacterium smegmatis* MC$^2$155, *Pseudomonas aeruginosa*, *Bacillus subtilis* MTCC-121, *Mucobacterium smegmatis* MC$^2$155 Wld type, *Mucobacterium smegmatis* MC$^2$155 (NaiR) 6b, *Mucobacterium smegmatis* MC$^2$155 13a and *E. Coli* DH5a.

8. A pharmaceutical composition for inhibiting the growth of bacterial pathogens, comprising an effective amount of the bioactive fraction obtained by the process of claim 1.

9. The composition as claimed in claim 8, wherein the said bioactive fraction may be administered systematically or orally and preferably orally.

10. The composition as claimed in claim 9, wherein the said bioactive fraction is administered singularly or in combination thereof to the patient.

11. The composition as claimed in claim 8, wherein the bioactive fraction is administered to the patient in combination with a pharmaceutically acceptable additives carriers, diluent, solvent, filter, lubricant, excipient, binder or stabiliser.

12. The composition as claimed in claim 8, wherein the additive used is selected from a group consisting of citric acid, calcium carbonate, magnesium hydroxide gel and/or gel and/or lactose.

13. The composition as claimed in claim 8, wherein the daily dosage for humans is in the range of 500 mg to 1000 mg.

14. The composition as claimed in claim 8, wherein the amount of the bioactive fraction in the composition is in the range of 100 mg to 500 mg.

15. A pharmaceutical composition useful for treating fluoroquinolone resistant bacterial infections including enteric and systemic infections, said composition comprising 10 to 50% by wt of the root extract of vetiver obtained by the process of claim 1, 0.4 to 1% by wt of citric acid, 10 to 20% by wt of calcium carbonate, 10 to 20% by wt of magnesium hydroxide gel, 20 to 60% by wt of lactose and optionally comprising other pharmaceutically acceptable additives.

16. The pharmaceutical composition as claimed in claim 15 is optionally compounded with honey by dispersing the constituents in honey.

17. A method of treating a patient with bacterial infection said method comprising administering a pharmaceutically dosage of a bioactive fraction or a formulation comprising a bioactive fraction or a lyophilised extract of plant *Vetiveria zizanioides* obtained by the process of claim 1.

18. A method as claimed in claim 17 wherein said bioactive fraction may be administered systematically or orally and preferably orally.

19. A method as claimed in claim 18, wherein the said bioactive fraction is administered singularly or in combination thereof to the patient.

20. A method as claimed in claim 17, wherein the bioactive fraction is administered to the patient in combination with a pharmaceutically acceptable additive, carrier, diluent, solvent, filter, lubricant, excipient, binder or stabiliser.

21. A method as claimed in claim 17 wherein the additive used is selected from a group consisting of citric acid, calcium carbonate, magnesium hydroxide gel and/or gel and/or lactose.

22. A method as claimed in claim 17, wherein the daily dosage for humans is in the range of 100 mg to 500 mg.

23. A method as claimed in claim 17, wherein the preferred dosage is in the range of 150 mg to 250 mg.

* * * * *